United States Patent
Horie et al.

(10) Patent No.: US 10,539,584 B2
(45) Date of Patent: Jan. 21, 2020

(54) SAMPLING NOZZLE, AUTOMATIC ANALYZER USING THE SAME, AND METHOD OF MANUFACTURING SAMPLING NOZZLE

(71) Applicant: HITACHI HIGH-TECHNOLOGIES CORPORATION, Tokyo (JP)

(72) Inventors: Yosuke Horie, Tokyo (JP); Tomohiro Inoue, Tokyo (JP); Hitoshi Tokieda, Tokyo (JP); Takamichi Mori, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 152 days.

(21) Appl. No.: 15/534,628

(22) PCT Filed: Dec. 7, 2015

(86) PCT No.: PCT/JP2015/084227
§ 371 (c)(1),
(2) Date: Jun. 9, 2017

(87) PCT Pub. No.: WO2016/098622
PCT Pub. Date: Jun. 23, 2016

(65) Prior Publication Data
US 2017/0370957 A1    Dec. 28, 2017

(30) Foreign Application Priority Data
Dec. 18, 2014    (JP) .................. 2014-255707

(51) Int. Cl.
*G01N 35/10*    (2006.01)
*G01N 1/10*    (2006.01)

(52) U.S. Cl.
CPC ........... *G01N 35/1079* (2013.01); *G01N 1/10* (2013.01)

(58) Field of Classification Search
CPC ........ G01N 35/00; G01N 35/04; G01N 35/10; G01N 1/00
See application file for complete search history.

(56) References Cited

FOREIGN PATENT DOCUMENTS

| CA | 2130129 A1 | 3/1995 |
|----|------------|--------|
| JP | 07-191040 A | 7/1995 |

(Continued)

OTHER PUBLICATIONS

Extended European Search Report received in corresponding European Application No. 15869827.4 dated Jul. 5, 2018.

(Continued)

*Primary Examiner* — David M. Gray
*Assistant Examiner* — Andrew V Do
(74) *Attorney, Agent, or Firm* — Mattingly & Malur, PC

(57) ABSTRACT

A CTS nozzle achieves the object of reducing rubber chips produced when the CTS nozzle is inserted into and extracted from a rubber plug of a sample container during dispensing of a sample, thereby inhibiting the wear of the tip of the CTS nozzle. The CTS nozzle has two cut surfaces at its tip, and the pressure applied from the rubber when the nozzle is inserted into the rubber plug is dispersed onto the two cut surfaces without being deflected onto one of the cut surfaces. The pressure applied to the nozzle due to the resilience of the rubber being pushed away by the nozzle is thus dispersed and the rubber chips produced by the friction between the cut surfaces of the nozzle and the rubber are reduced. As a result of the reduced friction, the wear of the tip of the nozzle is minimized.

9 Claims, 9 Drawing Sheets

(56) References Cited

FOREIGN PATENT DOCUMENTS

| | | |
|---|---|---|
| JP | 2003-166911 A | 6/2003 |
| JP | 2010-025804 A | 2/2010 |
| JP | 2011-167230 A | 9/2011 |
| JP | 3180120 U | 12/2012 |
| JP | 2014-066706 A | 4/2014 |
| WO | 98/04302 A1 | 2/1998 |
| WO | 2014/084731 A1 | 6/2014 |

OTHER PUBLICATIONS

International Search Report of PCT/JP2015/084227 dated Apr. 5, 2016.

(a)    (b)

(a)

SAMPLING NOZZLE, AUTOMATIC ANALYZER USING THE SAME, AND METHOD OF MANUFACTURING SAMPLING NOZZLE

TECHNICAL FIELD

The present invention relates to a sampling nozzle that, in an automatic analyzer to perform a componential analysis by mixing a sample such as blood serum or urine with a reagent, pierces a rubber plug sealing a sampling container to aspirate the sample in the container.

BACKGROUND ART

The container for a sample such as blood is sealed with a plug made of rubber or the like to prevent degradation and leakage of the sample. Some automatic analyzers using such a sample container are compatible with closed tube sampling (CTS) by which a sample can be dispensed and analyzed without having to unplug the sample container. The CTS-compatible automatic analyzer includes a dispensing mechanism having a nozzle with a sharp tip for piercing a rubber plug with a thickness of about 6 mm (hereinafter, also called CTS nozzle) to let the CTS nozzle pierce the plug to aspirate the sample in the container. The general CTS nozzle has the tip sharped by obliquely cutting one surface of the tip of a metal tube with a hollow as described in PTL 1.

In addition, some CTS nozzles have a needle-like blade at the tip of the hollow metallic tube and an opening for aspirating the sample on the side surface of the nozzle as described in PTLs 2 and 3.

Meanwhile, there is a method by which a paracentesis needle separately from a nozzle is provided to open the rubber plug and pass the nozzle through the opening in the rubber plug opened by the paracentesis needle to aspirate the sample as described in PTL 4.

CITATION LIST

Patent Literature

PTL 1: JP 7-506668 A
PTL 2: JP 2010-25804 A
PTL 3: JP 2014-66706 A
PTL 4: JP 3180120 U

SUMMARY OF INVENTION

Technical Problem

It is important that the CTS nozzle is structured to secure the dispensing accuracy and satisfy the following two conditions: the first is that the CTS nozzle can reduce the production of rubber chips when being inserted into the rubber plug; and the second is that the nozzle has a long lifetime.

For example, in the CTS as described in PTL 1 in which the rubber plug in the sample container is pierced with the CTS nozzle to dispense the sample in the container, some rubber chips may be produced when the CTS nozzle is inserted into and extracted from the rubber plug. When any rubber chips attach to the CTS nozzle extracted from the rubber plug, the rubber chips may drop onto the analyzer during the movement of the nozzle or the discharge of the sample. The dropped chips, when being mixed into the sample in a reaction cell, may unfavorably influence the inspection accuracy. In addition, even if the rubber chips drop onto any place other than the reaction cell, the rubber chips contaminate the analyzer. It is thus desired to reduce the production of rubber chips when the CTS nozzle is inserted and extracted.

The rubber chips are likely to occur in the CTS nozzle described in PTL 1 because no structural balance between a conical taper angle 16 and a cut angle 18 is considered, and the load of insertion of the CTS nozzle into the rubber plug is deflected to the surface on the cut angle 18 side. Accordingly, deflected rubber pressure is applied to the cut angle 18 side. The force of friction between the rubber and the nozzle becomes stronger at the time of the insertion due to the deflected rubber pressure, and as a result, the rubber is likely to be shaved and rubber chips are produced. Therefore, the nozzle described in PTL 1 is comparatively likely to produce the rubber chips, and the issue of the rubber chips is not considered or solved.

In addition, after dispensing, the inside and outside of the CTS nozzle in the automatic analyzer are cleaned for repeated use, and the CTS nozzle may treat several thousand of samples a day. To handle an increased number of inspections, the nozzle needs to be inserted into and extracted from the rubber plug at high speeds, and the tip of the nozzle is gradually worn and the nozzle becomes lowered in the capability of cutting and opening a rubber plug. Therefore, there is demand for the nozzle with the tip less prone to be worn.

Meanwhile, the nozzle with the needle-shaped tip as described in PTLs 2 and 3 has an aspiration port on the side surface, thereby presenting other substantive problems that, when the aspirated sample is discharged, the sample is not favorably cut (deterioration in the dispensing accuracy) and the inside of the nozzle can be unevenly cleaned.

In particular, PTL 3 discloses that the tilt and area of the nozzle are selected such that force components cancel each other out in the radial direction in the region of a tip 8. The nozzle described in PTL 3 can be expected to be effective in reducing frictional force to some degree with consideration of the structural balance in the nozzle. However, a surface 26 is not disposed at the needle tip, and the structural balance in the true needle tip is not considered. When the structural balance is not truly achieved in the needle tip, that is, when the load of local force at the needle tip is not properly dispersed, the force is slightly deflected. As a result, the needle is inserted in a slightly tilted state. Consequently, the nozzle tip is more likely to wear as compared to the case where the nozzle is vertically inserted. This results in local increase in the force of friction between the rubber and the nozzle, thereby leading to easy production of rubber chips.

According to PTL 4, there is the need to provide a dedicated needle for opening the rubber plug and a mechanism for driving the needle upward and downward, which results in apparatus complexity and cost increase.

As described above, none of the conventional CTS nozzles are structured to secure the dispersing accuracy and satisfy sufficiently the reduction of rubber chips and comparatively longer lifetime of the nozzle. The inventor has contemplated solving these problems at the same time because future faster insertion of the nozzle into the rubber plug would make the problems more obvious. The inventor has performed earnest studies and devised a CTS nozzle of a structure as disclosed in the examples.

An object of the invention is to provide a CTS nozzle that withstands repeated use and produces few rubber chips.

Solution to Problem

Representative examples of the invention are as follows:
The present invention is a cylindrical sampling nozzle for piercing a sampling container with rubber to aspirate a sample in the container, and the nozzle includes: a hollow extending lengthwise of the sampling nozzle, the hollow including an opening for aspirating the sample; a first surface disposed at an end of a tube having the hollow, the first surface having a plane surrounding the opening; a second surface disposed opposite the first surface; and a tip of the sampling nozzle formed by an intersection line of the first surface and the second surface, wherein: the hollow which is not bent near the tip includes the opening; the second surface has a curved surface that is curved in a circumferential direction of the cylindrically-shaped and is tilted linearly lengthwise of the sampling nozzle; and a distance between the tip of the sampling nozzle and an end of the second surface on a root side of the second surface of the sampling nozzle is shorter than a distance between the tip of the sampling nozzle and an end of the first surface on a root side of the first surface of the sampling nozzle.

In the sampling nozzle (CTS nozzle) of the invention, the nozzle tip as a true needle tip has the two shaved surfaces (hereinafter, called cut surfaces or surfaces) so that, when the nozzle is inserted into the rubber plug, the pressure from the rubber (the force with which the nozzle is pressed against the rubber) is not deflected to one surface of the nozzle but is dispersed to the two surfaces of the nozzle (the first surface and the second surface). Since the pressure from the rubber is dispersed, the force with which the shaved surfaces of the nozzle are pressed against the rubber becomes small to reduce the production of the rubber chips caused by the friction between the shaved surfaces of the nozzle and the rubber. The reduction in the friction with the rubber suppresses wear of the nozzle tip.

In addition, a manufacturing method according to the present invention includes the steps of: (a) preparing a tube having a hollow extending lengthwise of the tube; (b) forming a curved surface at an end of the tube, wherein the curved surface is curved in a circumferential direction of the cylindrically-shaped without bending the hollow, axisymmetric with respect to an axis of the tube, and linearly tilted lengthwise of the tube; and (c) linearly machining the tube using a plane including a first point on the curved surface and a second point on the further root of the tube rather than the area on the curved surface where the first point is disposed, thereby forming the end of the sampling nozzle using the surface surrounding the hollow and further using an intersection line with the curved surface.

As described above, providing the nozzle tip with the two shaved surfaces equivalent to the first and second surfaces makes it possible to suppress the production of rubber chips and lengthen the lifetime of the cut surfaces of the nozzle that would have been worn due to the friction with the rubber.

Advantageous Effects of Invention

According to the invention, it is possible to, in an automatic analyzer compatible with CTS by which to pierce a rubber plug and aspirate directly a sample in a container, reduce the production of rubber chips when a CTS nozzle is inserted to and extracted from the rubber plug and lengthen the lifetime of the nozzle.

DESCRIPTION OF EMBODIMENTS

An embodiment of the invention is hereinafter described with reference to FIGS. 1 through 9.

Figure 1:
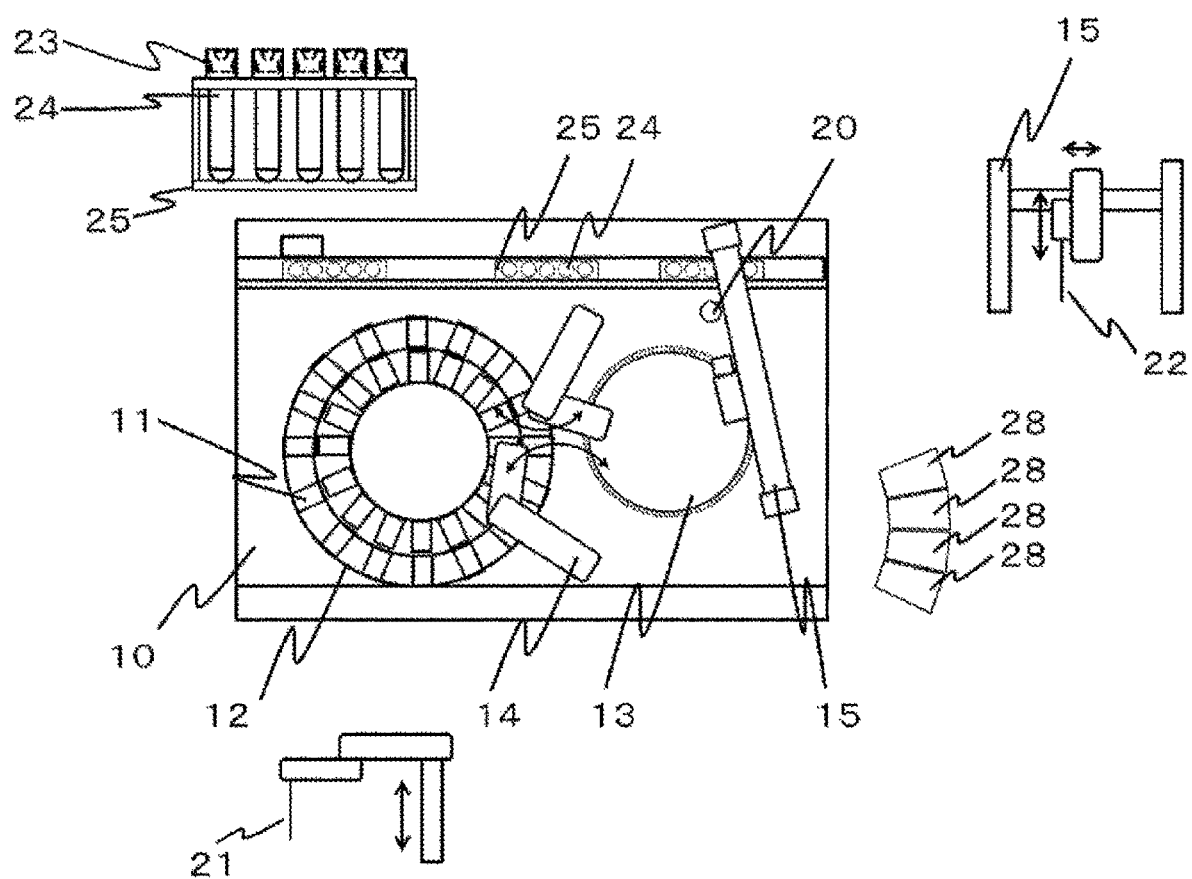
FIG. 1 is a plan view of an automatic analyzer for direct dispensing from a sealed container according to the present invention.
Figure 2:
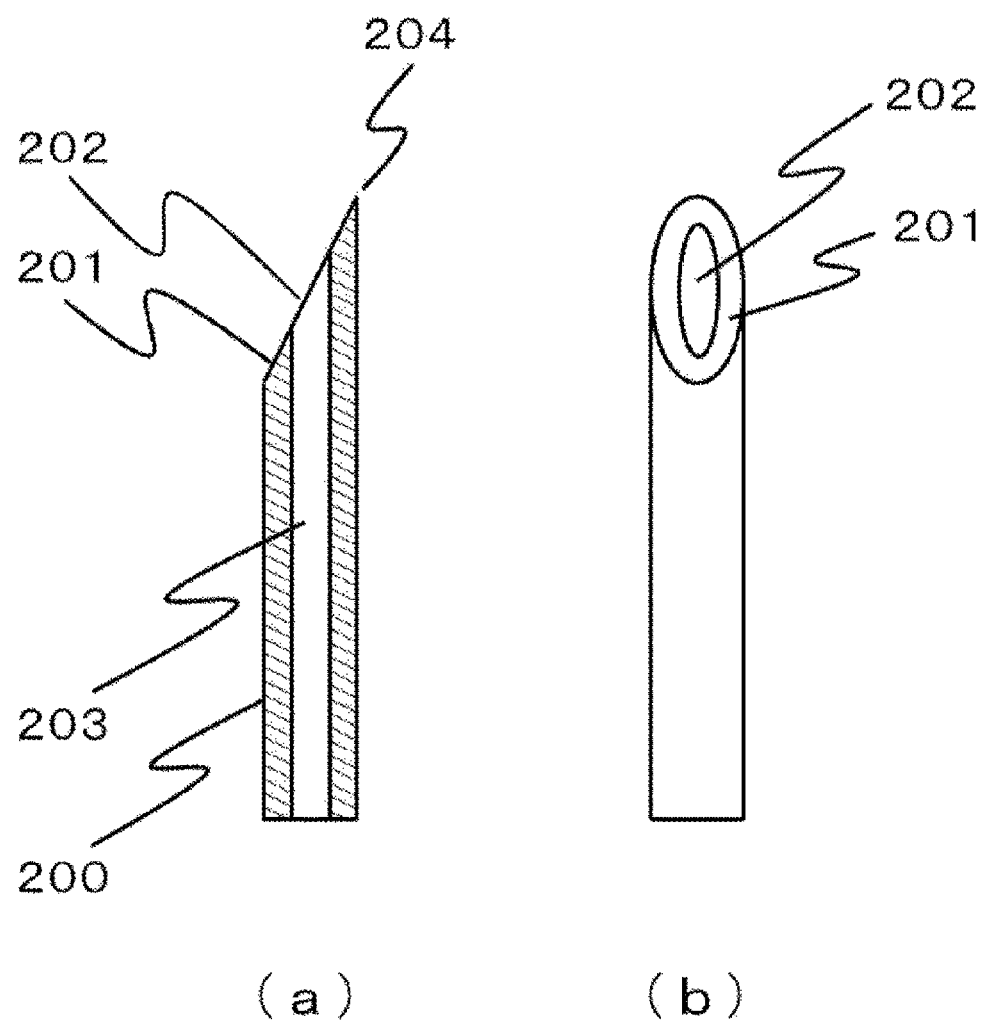
FIG. 2 shows a cross-sectional view and an external appearance view which illustrate the tip of a general CTS nozzle.

FIG. 1 is a diagram illustrating a configuration of an automatic analyzer of the invention. An automatic analyzer 10 includes: a reagent disk 12 that is loaded with a plurality of reagent containers 11; a reaction disk 13 in which a reagent and a sample are mixed and the reaction of the mixture is measured; a reagent dispensing mechanism 14 that aspirates and discharges the reagent; and a sample dispensing mechanism 15 that aspirates and discharges the sample. The reagent dispensing mechanism 14 includes a reagent nozzle 21 for dispensation of the reagent, and the sample dispensing mechanism 15 includes a CTS nozzle 22 for dispensation of the sample. The sample introduced into the analyzer is sealed in a sample container (test tube) 24 closed with a rubber plug 23, and is loaded into a rack 25 and carried. The rack 25 includes a plurality of sample containers 24. The sample is a blood-originated sample such as blood serum or whole blood, or urine.

The sample dispensing mechanism 15 moves the CTS nozzle 22 to an aspiration position where to aspirate a sample from the sample container 24, a discharge position where to discharge the sample into a cell 28, and a cleaning position where there is a cleaning vessel 20 to clean the tip of the CTS nozzle 22. Further, the sample dispensing mechanism 15 moves the CTS nozzle 22 down to respective heights of the sample container 24, the reaction cell 13, and the cleaning vessel 20 at the aspiration position, the discharge position, and the cleaning position. During the descending operation of the sample container 24, the CTS nozzle 22 is pierced into the rubber plug 23 of the sample container 24 so that the tip of the CTS nozzle 22 is inserted into the sample in the sample container 24 to aspirate the sample. The tip of the CTS nozzle 22 is sharpened to pierce the rubber plug 23 in order to pierce the CTS nozzle 22 into the rubber plug 23 for direct dispensation without removing the rubber plug 23 as described above.

To perform the foregoing operation, the sample dispensing mechanism 15 is configured to move the CTS nozzle 22 vertically and horizontally. The CTS nozzle 22 is cleaned after dispensation of one sample, and then dispenses another sample. In this manner, the CTS nozzle 22 is repeatedly used for dispensation.

After aspiration of a sample, the sample is discharged into the cell 28. A liquid mixture of the sample and a reagent in the cell 28 is optically measured to calculate the concentration of a predetermined component included in the sample. The details of analysis by an automatic analyzer are publicly known and therefore detailed descriptions thereof are omitted here.

FIGS. 2(a) and 2(b) are examples of a cross-section view and an external view of the tip of a general CTS nozzle, respectively. A general CTS nozzle 200 is made from a hollow metallic tube and has the tip obliquely cut and sharpened with a cut surface 201. Due to the cutting, the tip of the CTS nozzle 200 has an elliptic opening 202 through which a sample is aspirated and discharged. In addition, the general CTS nozzle 200 has at the root side a portion (not illustrated) to connect to a pipe. A hollow 203 of the CTS nozzle 200 connects to a pipe filled with water, and the pipe further connects to a pump (not illustrated). The pressure in the hollow 203 of the general CTS nozzle 200 can be changed by the operation of the pump, whereby the CTS nozzle 200 can aspirate and discharge the sample.

As described above, the nozzle is repeatedly pieced into the rubber plug. Accordingly, a tip portion 204 of the CTS nozzle 200, when it is too sharpened, will be small in thickness and likely to be chipped. Therefore, the tip portion 204 needs to have a certain degree of thickness, and in particular, the tip of the CTS nozzle 200 installed in an apparatus where the tip is to be repeatedly inserted into the rubber plug 23 at high speeds is less acute-angled as compared to an injection needle that would be used only once.

Figure 3:
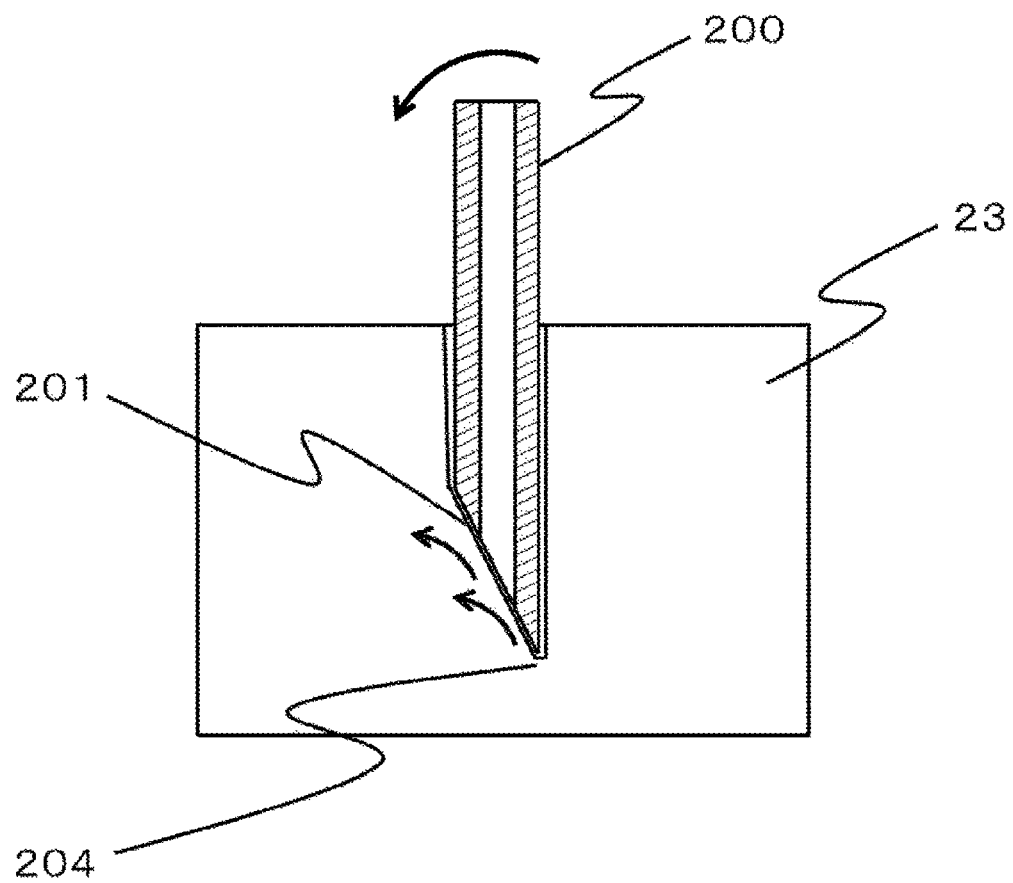
FIG. 3 is a cross-sectional view when the general CTS nozzle is inserted into a rubber plug.
Figure 4:
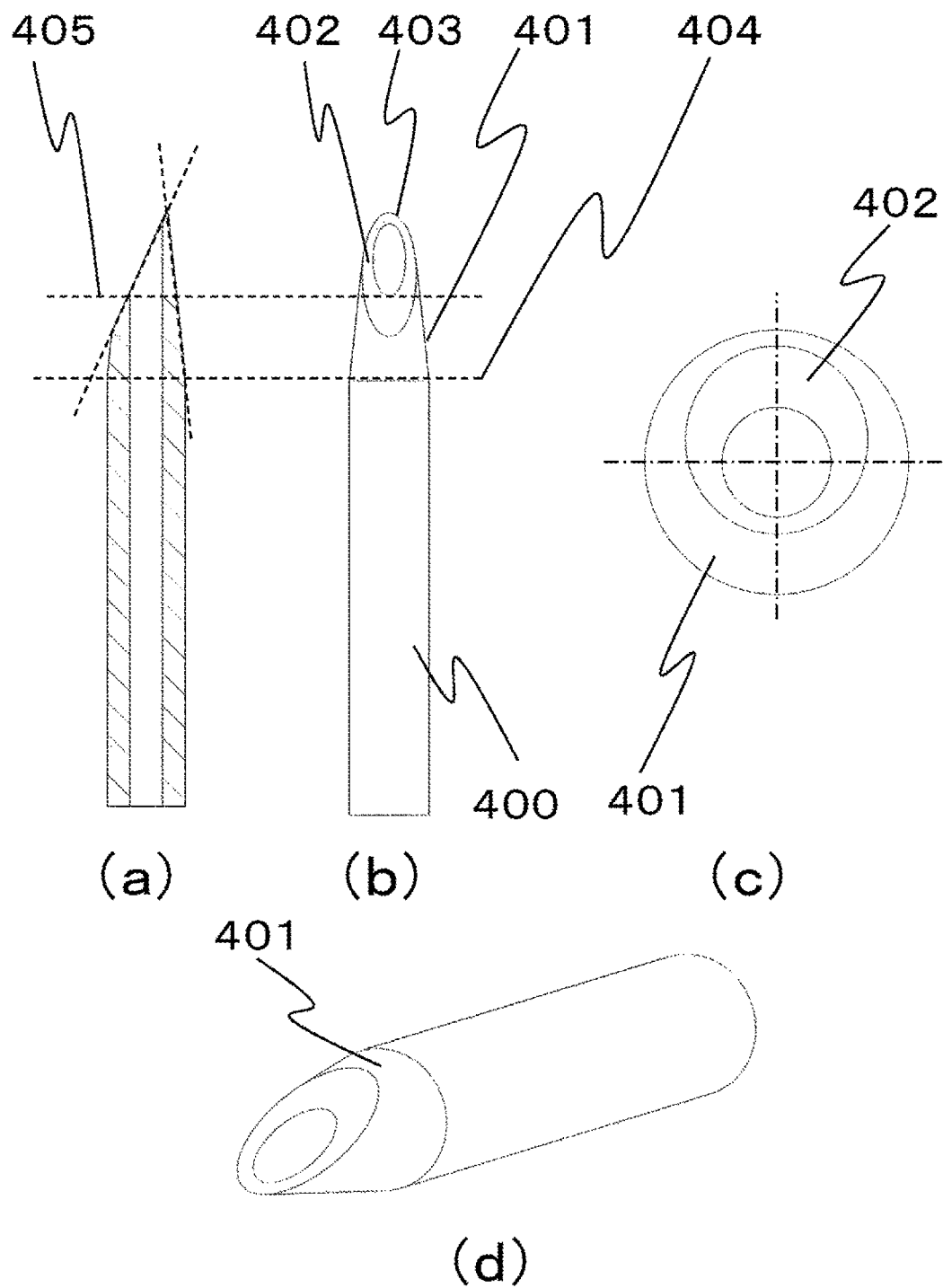
FIG. 4 shows cross-sectional views and external appearance views which illustrate the tip of the general CTS nozzle.
Figure 5:
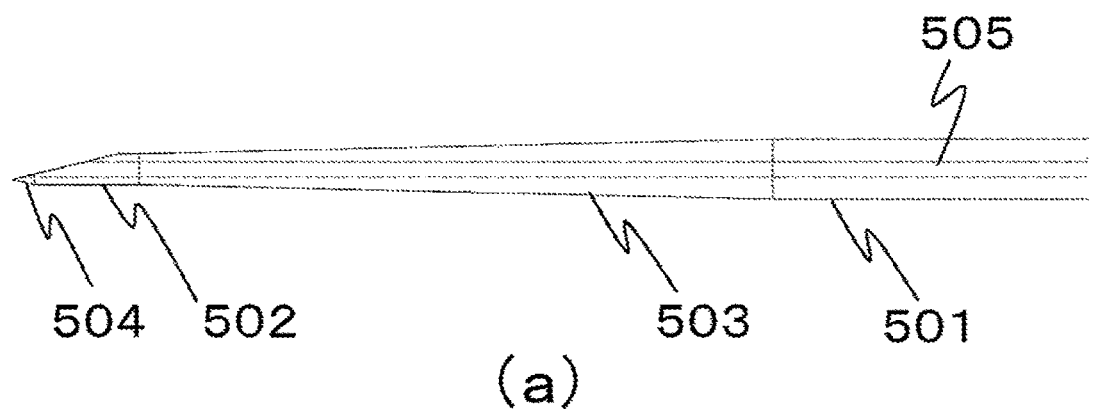
FIG. 5 shows one example of the shape of a CTS nozzle according to the present invention.
Figure 5:
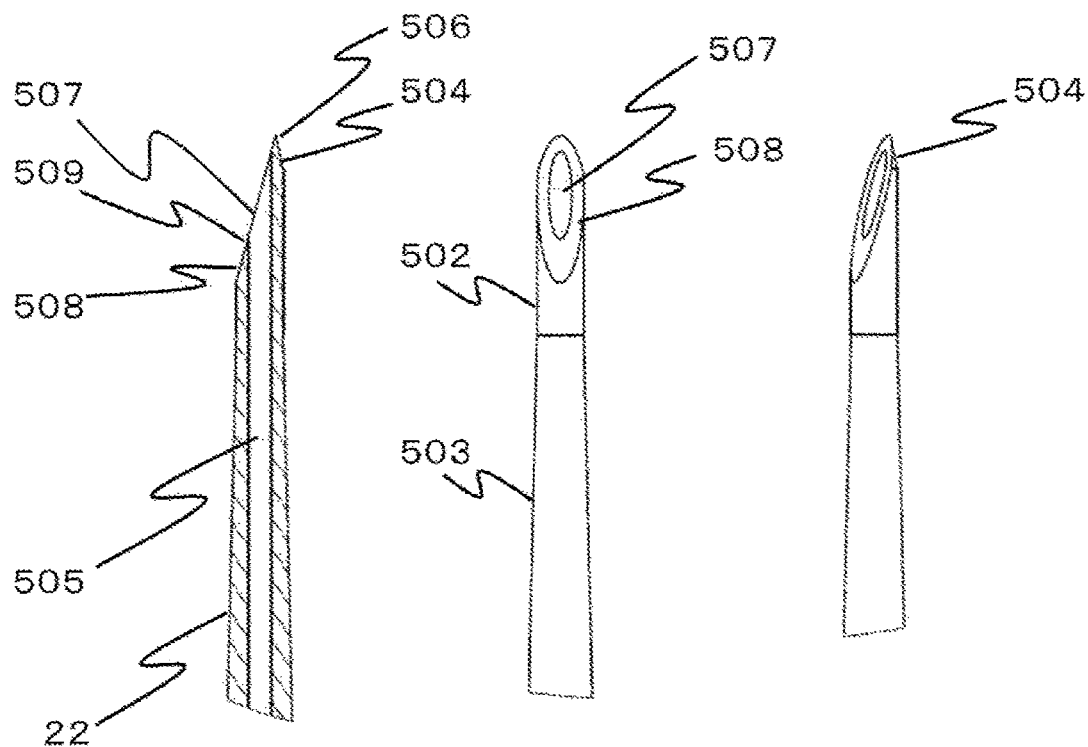
Figure 6:
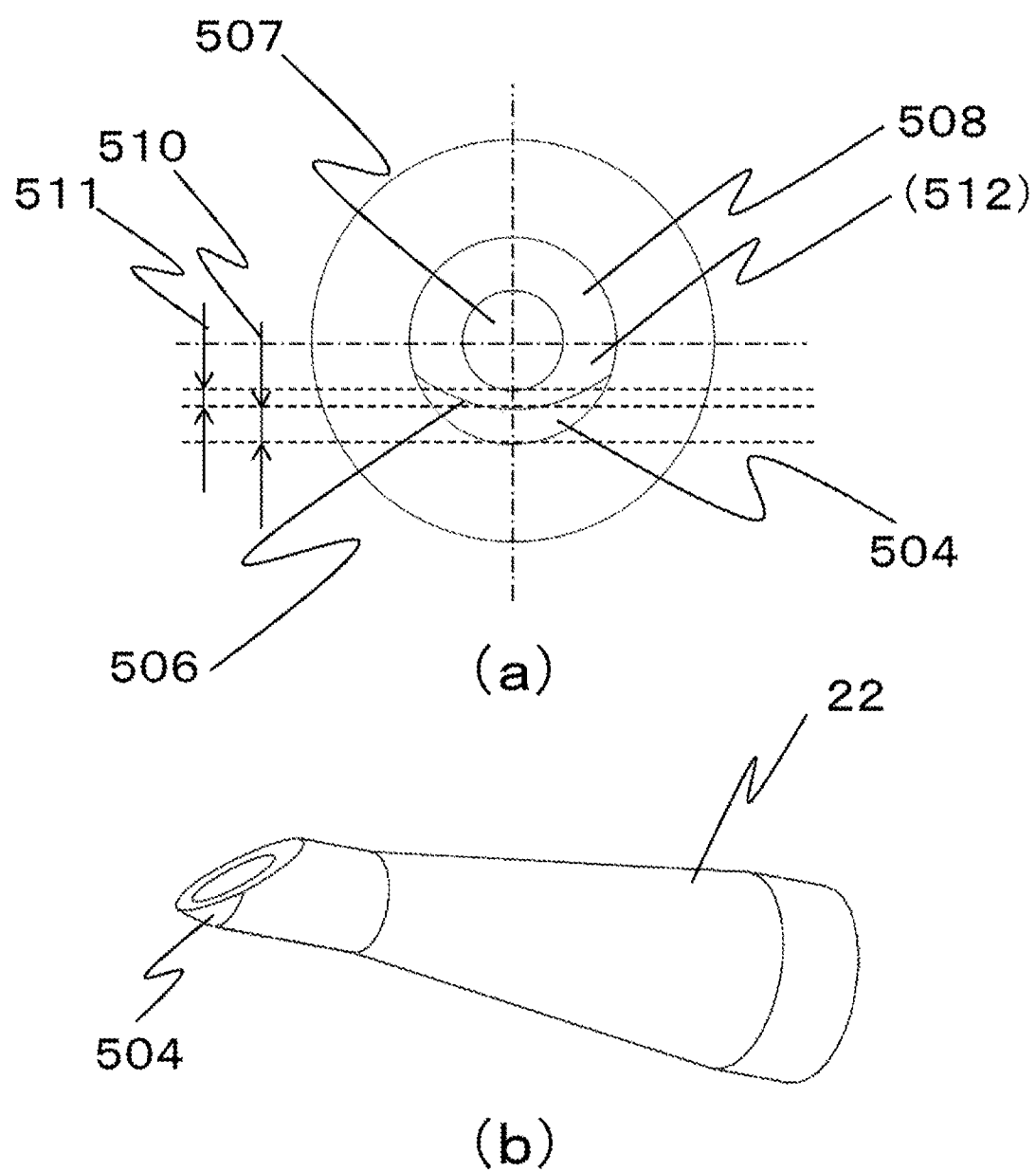
FIG. 6 shows one example of the shape of the CTS nozzle according to the present invention.

FIG. 3 is a cross-sectional view of the general CTS nozzle 200 inserted into the rubber plug 23. The tip portion 204 of the CTS nozzle 200 cuts into the rubber plug 23, and the obliquely cut surface 201 pushes away the rubber, and then the CTS nozzle 200 passes through the rubber while widening the cut portion of the rubber plug 23. The rubber pushed away by the cut surface 201 puts pressure on the cut surface 201 by its resilience. However, since the CTS nozzle 200 has the cut surface 201 on one side, the rubber deforms more largely on the cut surface 201 side, and the pressure from the rubber is deflected to the cut surface 201 side of the CTS nozzle 200. This generates strong frictional force between the cut surface of the rubber plug 23 and the cut surface 201. Further, the cut surface 201 of the CTS nozzle 200 is generally cut by a laser beam machine or the like and is rougher than the side surface of the CTS nozzle 200, thereby easily producing rubber chips by friction with the rubber plug 23. In addition, due to the frictional force described above, the CTS nozzle 200 tends to be obliquely inserted into the rubber.

FIGS. 4(a) to 4(d) illustrate one example of a CTS nozzle 400 different from the one illustrated in FIG. 3 (CTS nozzle 200). For example, the CTS nozzle 400 is a nozzle with a conical taper as described in PTL 1 (the taper obtained at the conical taper angle 16 described in PTL 1). FIG. 4(a) is a cross-sectional view of the tip of the CTS nozzle, FIG. 4(b) is an external side view of the same, FIG. 4(c) is an external view of the same seen from an opening, and FIG. 4(d) is a perspective view of the same.

The CTS nozzle 400 has a taper 401 at the tip portion of a hollow metallic tube, and has a cut surface 402 by obliquely cutting and sharpening a tip 403. The provision of the taper 401 at the tip portion makes it possible to reduce the load during passage through the rubber. However, when the taper length is short, the rubber is sharply deformed by the insertion of the nozzle, and the nozzle is placed under strong pressure from the rubber to increase the insertion load and produce rubber chips. Accordingly, with the shape of the CTS nozzle 400, a taper end 404 needs to be positioned closer to the root side of the nozzle than a tip cut end 405 for a smaller taper angle. However, when the taper angle is decreased (the taper length is increased), the rubber hits against mostly the cut surface 402 side of the CTS nozzle 400 and the tip of the CTS nozzle 400 produces chips as in the case of the CTS 200. In addition, the CTS nozzle 400 has the taper 401 at the entire tip portion, and the tip is thin on the whole and is likely to be chipped due to repeated use.

FIGS. 5(a) to 5(d) illustrate one example of the CTS nozzle shape of the invention. In the CTS nozzle 22, a root-side straight portion 501 has an outer diameter of φ1.6 mm, a tip-side straight portion 502 (3.5 mm from the tip) has an outer diameter of φ0.8 mm, an intermediate tapered portion 503 between the root-side straight portion 501 and the tip-side straight portion 502, a tip-side tapered portion 504 closer to the tip side than the tip-side straight portion 502, and a straight hollow 505 in the inside (FIG. 5(a)). The hollow 505 extends lengthwise of the CTS nozzle. FIG. 5(b) is a cross-sectional view, and FIGS. 5(c) and 5(d) are external views. The root-side straight portion 501 is cylindrical in shape, and the tip-side straight portion 502 is cylindrical in shape except for the tapered portion. Therefore, the sampling nozzle is basically cylindrical in shape. The term straight portion here refers to a cylindrical shape in which opposed lines of the outer surface and the cross section are almost parallel to each other in the cross-sectional view. The term straight hollow here refers to a cylindrical hollow in which opposed boundary lines between the hollow and the tube are almost parallel to each other in the cross-sectional view.

The root side of the CTS nozzle 22 connects to a pipe as with the general CTS nozzle 200, and the CTS nozzle 22 aspirates and discharges a sample by the operation of the pump.

When the CTS nozzle 22 is inserted into the rubber plug 23, the resilience of the deformed rubber acts as pressure on the CTS nozzle 22 as described above in relation to the example of the general CTS nozzle 200. The sample dispensing mechanism 15 loaded with the CTS nozzle 22 inserts the CTS nozzle 22 into the rubber plug 23 at high speeds (90 to 300 mm/s). However, when the tapered portion 503 is short, the rubber needs sharp deformation, and as the pressure acting on the CTS nozzle increases, the load at the time of insertion increases. Accordingly, the tapered portion 503 is desirably as long as possible and is preferably 20 mm or more, for example.

The CTS nozzle 22 of the invention has at the tip the tip-side tapered portion 504, and the tip of the tip-side straight portion 502 is obliquely shaved at a cut surface 508 and the shaved surface of the tip-side tapered portion 504 to make a tip portion 506 of the CTS nozzle 22 sharpened as described above (see FIG. 5(b)). The cut surface 508 is a cut surface with an elliptic opening 507. The cut surface 508 is disposed at the end of the tube with a hollow, and constitutes a cut surface having a flat plane surrounding the opening 507 (first surface). The tip-side tapered portion 504 is a tapered portion disposed on the side opposite to the cut surface (second surface). The tip portion 506 is a tip portion formed by intersection lines of the cut surface 508 (first surface) and the tip-side tapered portion 504 (second surface). Reference sign 508 represents the cut surface in particular because the tube is cut by the surface, but the cut surface here has the same meaning as the shaved surface, and therefore reference sign 508 is also used for the shaved surface.

The hollow 505 includes the opening 507 to aspirate the sample, and is not bent near the tip portion to prevent degradation of the dispensing accuracy.

The angle of the tip portion 506 of the CTS nozzle 22 is determined by the cutting angle of the cut surface 508 and the angle of the tip-side tapered portion 504, and is desirably around 27.5 degrees (the angle will be described later in detail).

The cut surface 508 of the CTS nozzle 22 is cut by a cutting machine such as a laser beam machine, for example, and is angled at an edge 509 of the shaved surface. The edge 509 of the shaved surface is preferably rounded (by blast polishing, for example) because, when the CTS nozzle 22 with the angled shaved surface is inserted into the rubber plug 23, the edge 509 of the shaved surface may shave the rubber and produce rubber chips.

In the case where the root-side edge 509 of the opening in the CTS nozzle 22 is acute-angled, when the CTS nozzle 22 is inserted into the rubber plug 23, the edge 509 acts as a blade on the rubber as with the tip portion 506. Accordingly, the root-side edge 509 of the CTS nozzle cuts the rubber entering into the opening 507 of the CTS nozzle 22 to clog the hollow 505 of the CTS nozzle 22. To prevent the clogging of the rubber plug 23 with rubber chips as well, the edge of the shaved surface of the CTS nozzle 22 is preferably rounded.

The feature of the invention is in providing the tip-side tapered portion 504 (second surface), which will be described below with reference to FIGS. 6(a) and 6(b).

FIGS. 6(a) and 6(b) are supplementary diagrams of one example of a CTS nozzle shape of the invention. FIG. 6(a) is a view of the CTS nozzle seen from the opening 507, and FIG. 6(b) is an enlarged perspective view of main components of the CTS nozzle.

First, the first feature of the CTS nozzle according to the invention is in the position of the root-side end of the shaved surface as the tip-side tapered portion 504. As illustrated in FIGS. 5(a), 5(b), 5(d), and 6(b), the end is positioned comparatively close to the tip side. The end is close to the tip because the thickness becomes smaller from the end toward the tip. This is advantageous in strength since the thinned portion can be shortened. Therefore, this configuration contributes to longer lifetime of the nozzle. It is important that at least the end is closer to the tip side than the end of the cut surface 508. Characteristically, the distance between the root-side end and the tip portion of the tip-side tapered portion 504 (second surface) of the CTS nozzle is shorter than the distance between the root-side end and the tip portion of the cut surface 508 (first surface) of the CTS nozzle. The compared distances are not distances on the tilted planes but are axial distances.

The second feature is in a curved surface of the tip-side tapered portion 504 forming the tip portion 506 with respect to the circumferential direction of the cylindrical shape. As illustrated in FIG. 6(a), the tip-side tapered portion 504 is curved with respect to the circumferential direction. Since the thinned portion is curved, the force from the cut surface 508 side is easier to disperse and the tip is less likely to be chipped as compared to the case where the tip-side tapered portion is planar. In addition, curving the tip-side tapered portion 504 increases the surface area to receive stronger force on the curved surface, whereby it is possible to keep an appropriate balance between the force applied to the cut surface 508 and the force applied to the tip-side tapered portion 504.

In addition, in the CTS nozzle 22 of the invention, the tip-side tapered portion 504 is curved to provide a wide blade at the tip 506 of the CTS nozzle 22. When the CTS nozzle 22 pierces the rubber plug 23, the rubber through which the CTS nozzle 22 passes is widened to the root diameter of the CTS nozzle 22 (1.6 mm in this example) or more. However, the rubber plug 23 is largely cut by the wide tip 506 so that the rubber can be widened with weak force. In particular, with the shape of the CTS nozzle 22 of the invention, the width of the blade at the tip 506 is the same as the outer diameter of the straight portion 502, and the straight portion 502 can be inserted into the rubber with weak force. Then, the tapered portion 503 widens moderately the rubber while passing through the rubber, and finally the root-side straight portion 501 with the largest outer diameter passes through the rubber. Accordingly, the rubber is not forcefully widened and this reduces the occurrence of rubber chips.

The third feature is in that the tip-side tapered portion 504 is linearly tilted with respect to the direction of the length of the CTS nozzle. As illustrated in FIGS. 5(a), 5(b), 5(d), and 6(b), the tip-side tapered portion 504 is linearly tilted with respect to the direction of the length. Since the cut surface 508 is a surface also linearly tilted with respect to the direction of the length, the rubber pressure can be easily dispersed to prevent the nozzle from being obliquely inserted. Preventing the oblique insertion decreases rubber chips and contributes to longer lifetime of the nozzle. For example, if the tip-side tapered portion 504 is not linearly tilted, the angle of the surface under the rubber pressure unstably varies depending on the depth of the insertion of the nozzle into the rubber, and the nozzle tends to be slightly obliquely inserted. In particular, in the structure of the same type as the nozzle of the invention in which the aspiration port points directly downward, the tip portion of the nozzle is deflected to the vicinity of the thick portion, and the dispersion of the rubber pressure becomes unstable immediately after the insertion into the rubber, which exerts a larger influence on the verticality of the nozzle insertion as compared to the nozzles described in PTLs 2 and 3 in which the tip portion is disposed near the center of the nozzle. Therefore, it is important that the tip-side tapered portion 504 is curved with respect to the circumferential direction and is linearly tilted with respect to the direction of the length.

These three features make it possible to increase the strength of the CTS nozzle, reduce the occurrence of rubber chips when the nozzle is inserted into and extracted from the rubber plug, and lengthen the lifetime of the nozzle.

The foregoing three aspects are the features of the CTS nozzle according to the invention, and the CTS nozzle is desirably configured as described below.

First, the tilt angle of the cut surface 508 is larger than the tilt angle of the tip-side tapered portion 504. This will be described later in detail with reference to FIG. 8.

In addition, when a distance 510 from the side surface of the straight portion 502 to the tip portion 506 and a distance 511 from the end of the hollow 505 to the tip portion 506 are defined, the position of the tip portion 506 as a blade is desirably selected such that the distance 510 is longer than the distance 511. In other words, when being seen from the opening 507 side, the tip portion 506 is positioned within the thick part of the nozzle, and is positioned closer to the opening 507 side than the outside of the thick part. This will be also described later.

It is desired to keep a balance in force dispersion by the difference in area between the tip-side tapered portion 504 and the cut surface 508. This will be also described later.

As illustrated in FIGS. 5(a) to 5(d), the nozzle includes the root-side straight portion, the tip-side straight portion smaller in the outer diameter than the root-side straight portion, and the tapered portion arranged between the root-side straight portion and the tip-side straight portion. The tip portion is desirably arranged at the tip of the tip-side straight portion.

The root-side straight portion, the tip-side straight portion, the tapered portion, and the tip portion are desirably made of the same material without being welded to one another.

Figure 7:
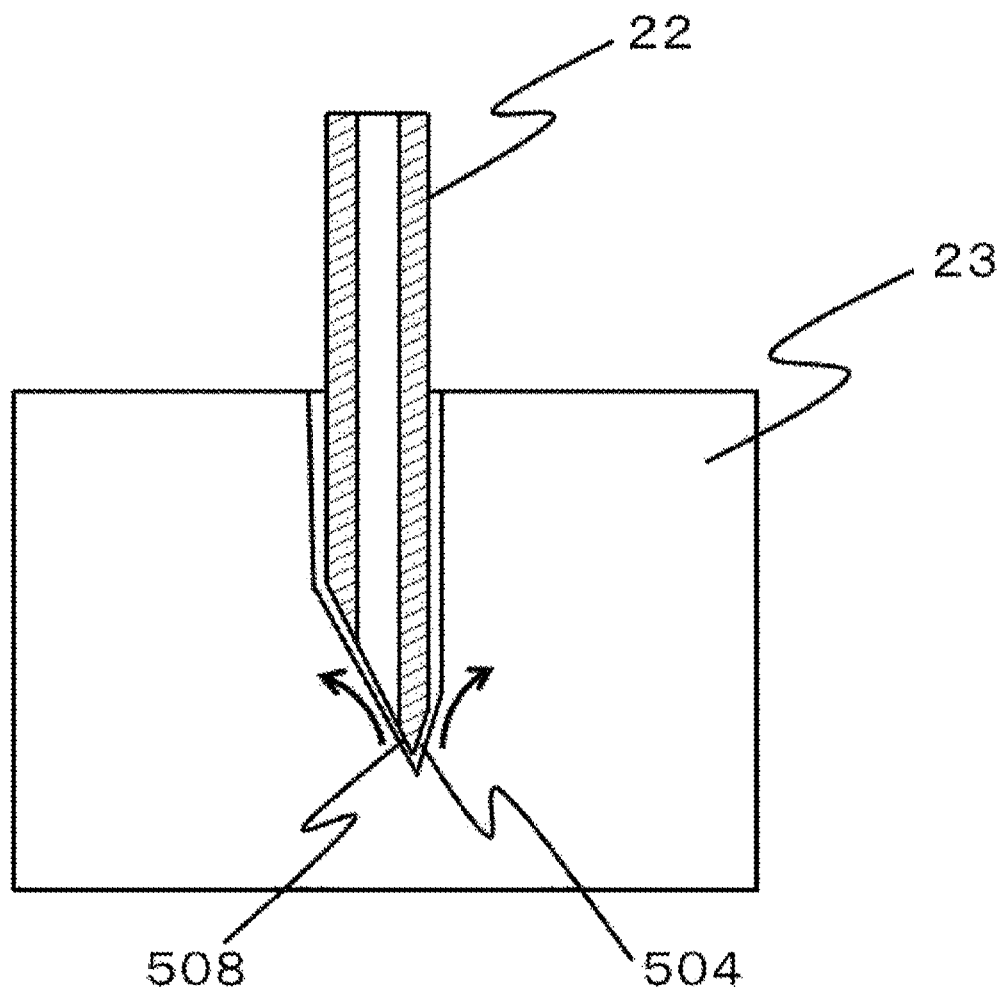
FIG. 7 is a cross-sectional view when the general CTS nozzle is inserted into the rubber plug.

FIG. 7 is a cross-sectional view of the CTS nozzle of the invention inserted into the rubber plug 23. When the CTS nozzle 22 of the invention is inserted into the rubber plug 23, the tip portion 506 cuts into the rubber. While the CTS nozzle 22 passes through the rubber, two surfaces of the tip-side tapered portion 504 and the cut surface 508 of the nozzle tip push away the rubber in their respective directions. The CTS nozzle 22 passes through the rubber while pushing and widening the cut portion of the rubber. When the CTS nozzle 22 passes through the rubber plug 23, the tip-side tapered portion 504 and the cut surface 508 of the nozzle tip receive pressure from the rubber by resilience of the rubber. However, the tip of the CTS nozzle 22 pushes away the rubber in a plurality of directions and the pressure from the rubber is dispersed. In addition, the rubber can be pushed away not only in the two right and left directions illustrated in the drawing but also in the forward and backward directions as illustrated by the right arrow in the drawing due to the curved surface of the tip-side tapered portion. The frictional force between the cut surface 508 and the rubber plug 23 is lower than that in the general CTS nozzle 200, thereby reducing rubber chips that would have produced by the friction between the shaved surface of the CTS nozzle and the rubber.

Further, by providing the two cut surfaces (504 and 508) at the tip of the CTS nozzle 22, the pressure from the rubber when the CTS nozzle 22 is inserted into the rubber plug 23 is unlikely to be deflected. This prevents the oblique insertion of the nozzle and allows the nozzle to be vertically inserted into the rubber plug 23. Particularly, it is possible to truly keep a structural balance in the tip portion and prevent the oblique insertion of the nozzle. In addition, dispersing the pressure from the rubber reduces the friction between the cut surface 508 of the CTS nozzle 22 and the rubber and suppresses the wear of the cut surface 508.

Figure 8:
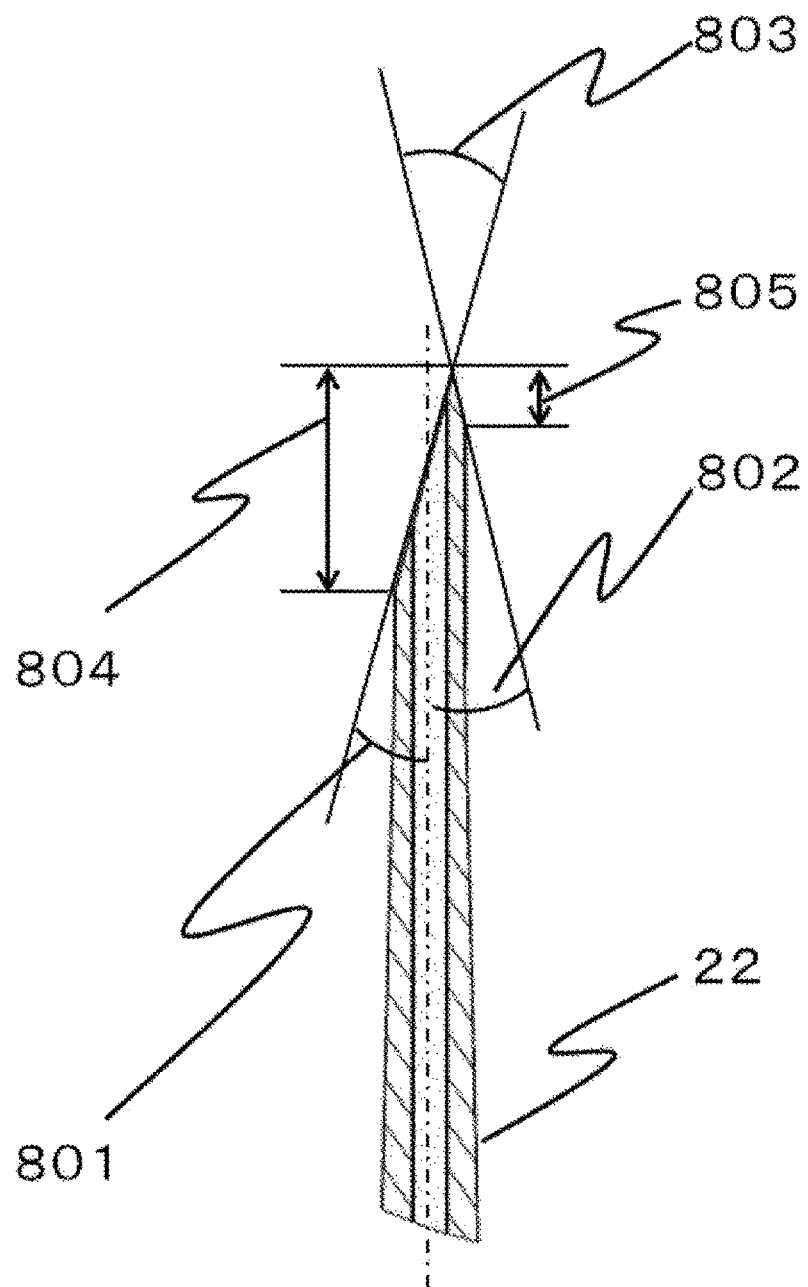
FIG. 8 shows definitions of angles of cut portions of the CTS nozzle according to the present invention.
Figure 9:
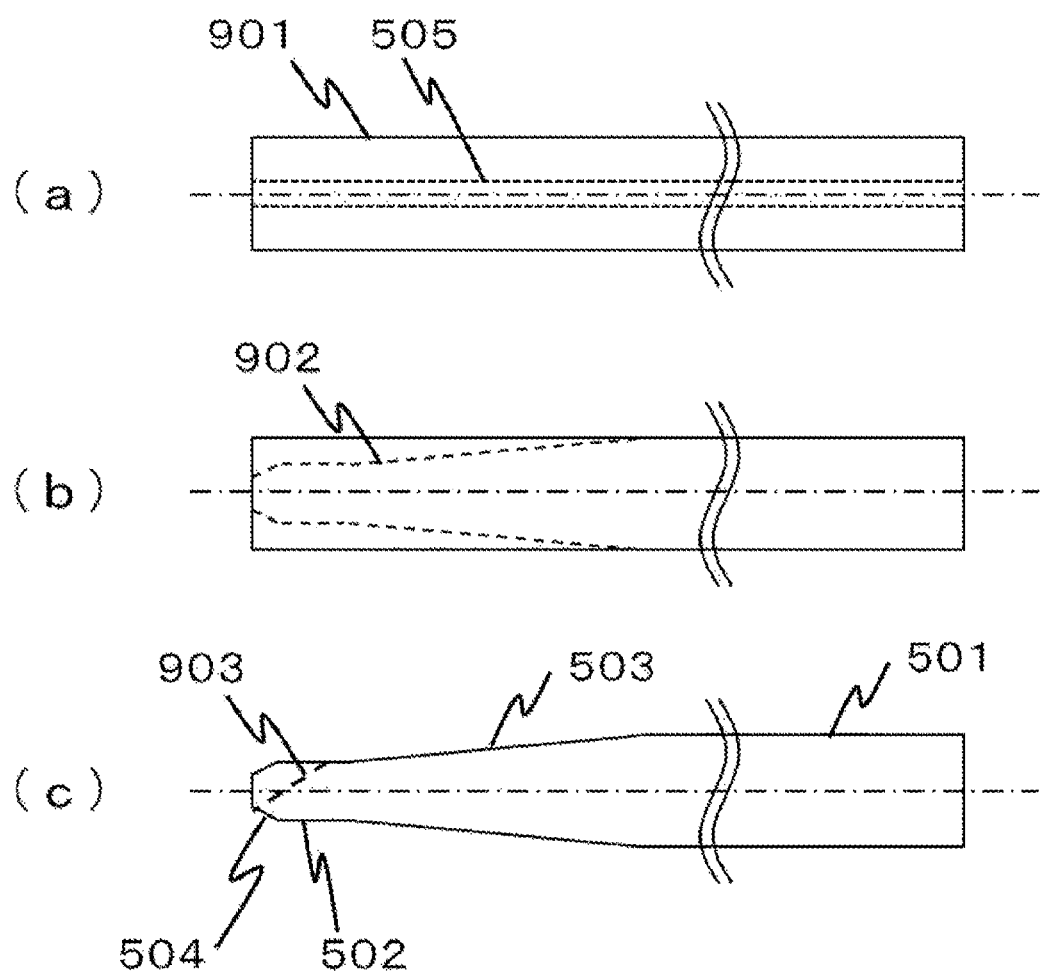
FIG. 9 shows one example of a procedure for manufacturing the CTS nozzle according to the present invention.

In addition, as described above, it is important that the tip-side tapered portion 504 is linearly shaped as seen in the cross-sectional view of FIG. 8. Since the cut surface 508 is linearly shaped and the tip-side tapered portion 504 as a rear surface is linearly shaped, the rubber pressure can be easily dispersed in a stable manner at the time of insertion of the nozzle tip to prevent the nozzle from being obliquely inserted.

The shape of the cut surface 508 will be described below. The cut surface 508 (first tapered portion) is a plane surrounding the opening 507. The opening 507 is elliptic in shape because it is formed by cutting obliquely the tube. Without the tip-side tapered portion 504, the outer circumference of the cut surface 508 would be elliptic in shape because the uniform thick portion is obliquely cut. However, the formation of the tip-side tapered portion 504 makes the cut surface 508 slightly shaved in the direction of the longer diameter of the opening 507. Specifically, the plane of the cut surface 508 is shorter on the tip portion side than on the root side in the direction of the long diameter of the opening 507. In this case, the lengths in the plane of the cut surface 508 are compared, and the length relationship can also be grasped from FIG. 6(a) in which the portion with reference sign 510 is shaved and the portion with reference sign 511 is left. In addition, the length relationship can also be grasped from FIG. 5(c) in which the root-side thick cut surface 508 is wide.

To obtain preferably the effect of rubber pressure dispersion as described above, the area of the tip-side tapered portion 504 and the area of the portion acting as the blade of the cut surface 508 at the nozzle tip (the portion ranging from the nozzle center to the nozzle tip 506 illustrated in FIGS. 6(a) and 6(b), hereinafter called a cut surface 512 of the nozzle tip) are preferably almost equal. This is because keeping an appropriate balance in the rubber pressure immediately after the insertion into the rubber plug 23 prevents the oblique insertion of the nozzle in an effective manner. For example, the difference between these areas is desirably kept within 0.1 mm$^2$.

In other words, the almost concentric elliptic cut surface 508 can be divided into a root side and a tip portion side by the short diameter of the elliptic opening 507. The difference between the area of the divided tip portion side and the area of the tip-side tapered portion 504 is desirably kept within 0.1 mm$^2$. Although the root-side area of the cut surface 508 generates deflected rubber pressure, the nozzle is inserted up to a certain degree, and the influence of the unbalanced rubber pressure on the oblique insertion of the nozzle can be ignored. In addition, since the tip-side tapered portion 504 (second surface) is curved in the circumferential direction as described above, the widely curved blade can be formed at the tip 506 of the CTS nozzle 22 to push away the rubber with weak force, and the influence of the unbalanced rubber pressure on the oblique insertion of the nozzle can be controlled to an ignorable degree.

FIG. 8 is a diagram defining the angle of the shaved portion in the CTS nozzle 22 of the invention. The CTS nozzle 22 of the invention has the tip-side tapered portion 504 at the nozzle tip 506 and the nozzle-tip cut surface 508 as described above. In the cross-sectional view of the CTS nozzle 22, the angle (tilt angle) formed by the straight line of the cut surface 508 and the centerline of the CTS nozzle 22 is defined as angle A (801), and the angle (tilt angle) formed by the straight line of the tip-side tapered portion 504 and the centerline of the CTS nozzle 22 is defined as angle B (802), and the tip angle of the CTS nozzle 22 is defined as angle C (803). The angle C (803) is the sum of the angle A (801) and the angle B (802). The length from the tip of the CTS nozzle 22 to the end of the cut surface 508 is defined as La (804), and the length from the tip of the CTS nozzle 22 to the end of the tip-side tapered portion 504 (second surface) is defined as Lb (805).

The tip portion 506 of the CTS nozzle 22 has the effect of pushing away the rubber to reduce the pressure on the cut surface 504 and reduce the production of rubber chips as described above. However, the production of rubber chips attributes to factors other than the friction with the cut surface 504. For example, the root-side edge 509 of the opening as a cause of clogging of the CTS nozzle 22 is acutely angled to shave the rubber and produce rubber chips. In addition, the tip portion 506 of the CTS nozzle 22 is obtusely angled to degrade cutting performance, and the tip portion 506 of the CTS nozzle 22 crushes and cuts the rubber and makes the cut end rough, thereby resulting in production of rubber chips. That is, the angle A (801) and the angle C (803) also relate to the production of rubber chips.

Table 1 shows the incidence of rubber chips when the CTS nozzles 22 with different combinations of the angle A (801) and the angle B (802) were inserted into and extracted from the rubber plug 23.

TABLE 1

| Condition No. | 1 | 2 | 3 | 4 | 5 | 6 | 7 | 8 | 9 |
|---|---|---|---|---|---|---|---|---|---|
| Angle A | 9.0 | 9.0 | 12.0 | 12.0 | 15.0 | 15.0 | 15.0 | 18.0 | 18.0 |
| Angle B | 12.0 | 13.5 | 12.0 | 13.5 | 12.0 | 13.5 | 15.0 | 13.5 | 15.0 |
| Angle C | 21.0 | 22.5 | 24.0 | 25.5 | 27.0 | 28.5 | 30.0 | 31.5 | 33.0 |
| Incidence of rubber chips | 29% | 43% | 29% | 29% | 0 | 0 | 43% | 29% | 57% |

Each of the CTS nozzles 22 under the conditions described in Table 1 was fixed to a mechanism capable of linear motion at a constant speed (150 mm/s), and the sample container 24 with the rubber plug 23 was fastened in the moving direction of the CTS nozzle 22. The CTS nozzle 22 was inserted into and extracted from the rubber plug 23 at a constant speed, and then was checked for the presence or absence of rubber chips left thereon. It can be seen from Table 1 that there were no rubber chips left under the conditions that the tip angle C (803) of the CTS nozzle 22 was 27.0 degrees and 28.5 degrees. Based on the results in Table 1, the CTS nozzle 22 with the angle A (801) of 15.0 degrees, the angle B (802) of 12.5 degrees, and the angle C (803) of 27.5 degrees (the angle A (801) was 15.0 degrees and the angle B (802) was 12.5 degrees) was prepared, inserted into and extracted from the rubber plug 23, and then checked for the rubber chips left. It has been revealed that there were no rubber chips left as in the cases under the conditions 5 and 6 described in Table 1.

It can be understood from the foregoing results that the tip angle C (803) desirably ranges from more than 25.5 degrees to less than 30.0 degrees to reduce rubber chips. The angle C (803) more desirably ranges from 26.0 degrees or more to 29.5 degrees or less, still more desirably ranges from 26.5 degrees or more to 29.0 degrees or less, and further still desirably ranges from 27.0 degrees or more to 28.5 degrees or less.

Next, the surface areas were checked. When the angle A (801) changes within a range of 9.0 to 18.0 degrees, the surface area of the cut surface 512 of the nozzle tip ranges from 0.39 to 0.97 mm$^2$ (the surface area becomes larger at a smaller angle). When the angle B (802) changes within a range of 12.0 to 15.0 degrees, the surface area of the tip-side tapered portion 504 ranges from 0.36 to 0.44 mm$^2$ (the surface area becomes smaller at a smaller angle). Although the surface areas of the cut surface 512 of the nozzle tip and the tip-side tapered portion 504 are preferably almost equal to obtain favorably the effect of dispersing the rubber pressure as described above, the tip angle C (803) is desirably set to less than 30.0 degrees from the results in Table 1 because the acute tip angle C 803 enhances the rubber cutting performance. According to the configuration of the invention, the tip angle C 803 can be adjusted by adjusting the angle formed by the cut surface 512 of the nozzle tip and the tip-side tapered portion 504.

With the angle A (801) of 15 degrees, the surface area of the cut surface 512 of the nozzle tip is 0.44 mm$^2$. With the angle B (802) of 12.5 degrees, the surface area of the cut surface 512 of the nozzle tip is 0.38 mm$^2$. These surface areas are almost equal at the angle C of the tip of 27.5 degrees and 29.5 degrees or less. The difference between the surface areas is 0.06 mm$^2$. The difference is desirably smaller without limit, but the difference of 0.1 mm$^2$ or less can be allowed. The value of the difference depends on the thickness of the CTS nozzle even with no change in the angle C (803) and constitutes an effective index for determining the thickness.

When the CTS nozzle 22 is inserted into the rubber, the effect of dispersing the rubber is determined by the surface areas and angles of the tip-side tapered portion 504 and the cut surface 512 of the nozzle tip. Accordingly, it is preferable that the angle A (801) and the angle B (802) are close to each other and the surface areas of the cut surface 512 and the tip-side tapered portion 504 are close to each other. To satisfy the foregoing conditions, the tip-side tapered portion 504 is positioned closer to the tip side than the root-side end of the opening 507 of the nozzle, and Lb (805) takes on a value smaller than La (804). The tip-side tapered portion 504 is positioned at the tip, and the root-side end of the tip-side tapered portion 504 is desirably positioned closer to the tip side than the center of the ellipse of the opening 507 (the point of intersection between the ellipse of the opening and the central axis of the nozzle).

To secure the surface area of the tip-side tapered portion 504, the distance 510 from the side surface of the straight portion 502 to the tip portion 506 and the distance 511 from the end of the hollow 505 to the tip portion 506 are desirably selected such that the distance 510 is longer than the distance 511 (see FIG. 6(a)). Further, the thin nozzle tip 506 would be more increasingly worn by repeated use, and thus the length Lb (805) is preferably shortened to secure the thickness. Accordingly, it is desired in the CTS nozzle 22 of the invention that the length Lb (805) is smaller than the length La (804), the angle A (801) is 15.0 degrees, and the angle B (802) falls within a range of 12.0 degrees or more to less than 15.0 degrees. Therefore, the angle A (801) is desirably larger than the angle B (802) as described above.

In addition, the CTS nozzle having the foregoing three features is especially effective in the dispersing operation with insertion into the rubber plug 23 at a high speed of 90 mm/s or more, for example, and desirably includes the specific structure as described above with reference to FIG. 8. In the case of the low-speed operation, the frictional force between the rubber and the nozzle becomes weak to make it less prone to cause the problem of rubber chips. As the speed is as higher as 100 mm/s or more or 150 mm/s or more, the influence of the frictional force becomes larger. Accordingly, the CTS nozzle is more effective when being used at the foregoing speeds or higher.

The CTS nozzle 22 desirably has at the tip portion the tip-side tapered portion 504 (and the cut surface 512), the straight portion 502, the tapered portion 503, and the straight portion 501 as illustrated in FIGS. 5(a) to 5(d). Accordingly, the acute-angled tip 506 cuts the rubber, then the tip-side tapered portion 504 and the cut surface 512 disperse the rubber, and then the tapered portion 503 moderately pushes away the rubber. Installing the CTS nozzle 22 in the sample dispensing mechanism 15 makes it possible to reduce the production of rubber chips at the time of insertion into and extraction from the rubber plug 23, and suppress the wear of the tip of the CTS nozzle 22 to lengthen the time until replacement is needed.

In the case of dispensing a minute quantity of sample, the sample may be discharged with the tip of the nozzle in contact with the cell 28. The shaved surface 508 is shaved by the tip-side tapered portion 504 and the tip of the shaved surface 508 is comparatively gently curved as seen from the shaved surface 508 side (see the tip illustrated in FIG. 5(c)). Since the gently curved tip can contact relatively widely the cell bottom, the CTS nozzle of the invention is suitable to the case of discharging a sample with the tip in contact with the cell. Contacting widely the cell bottom increases the area of contact between a discharged liquid drop and the cell bottom. Accordingly, it is possible to prevent appropriately the liquid drop of the sample from being brought back to the nozzle tip and facilitate the minute-quantity dispensation to the cell bottom. Therefore, the automatic analyzer is desirably configured to include a sample dispensing mechanism that discharges the sample in the CTS nozzle to the cell with the nozzle tip in contact with the bottom of the cell.

Next, a method of manufacturing the CTS nozzle will be explained.

FIGS. 9(a) to 9(c) illustrate one example of a method of manufacturing the CTS nozzle shape of the invention. The CTS nozzle 22 of the invention is manufactured by processing a metallic tube as with the general CTS nozzle 200, a stainless steel hollow tube (with an inner diameter of φ0.4 mm), for example. A straight tube 901 having the straight hollow 505 (see FIG. 9(a)) is a single component. The straight tube 901 is subjected to a shaving process 902 by a shaving machine such as a lathe to form the tip-side tapered portion 504, the tip-side straight portion 502, the root-side tapered portion 503, and the root-side straight portion 501 (see FIGS. 9(b) and 9(c)). The tube is shaved while being rotated around the axis, and thus the tube is seen in the same shape from any direction. The taper angle and surface shape of the tip-side tapered portion 504 are determined by this process. That is, the process needs to be performed taking the second and third features into account. The shape of the tip to be the tip-side tapered portion has a surface that is curved in the circumferential direction of the cylinder and is linearly tilted in the direction of the length. At this point in time, the tube is shaved while being rotated and the curved surfaces of the main portions constitute partial curved surface of the conical shape.

Next, the tube of the shape illustrated in FIG. 9(c) is subjected to a cutting process 903 by a cutting machine (such as a laser processing machine) to manufacture the CTS nozzle 22 of the invention illustrated in FIG. 5(a). This process needs to be performed taking the first feature into account. Specifically, in the cutting process 903, one cutting end is set in the portion closer to the root side than the tip-side tapered portion 504, and the other cutting end is set in the middle of the tilted surface of the tip-side tapered portion. The positions (510 and 511) of the nozzle tip 506 and the blade angle of the nozzle tip 506 can be determined by the processing angles in the shaving process 902 and the cutting process 903. In the foregoing processes, the CTS nozzle 22 can be manufactured by simple processing with few variations and at low cost. The root-side straight portion 501 may be prepared and welded as a separate member but is desirably cut out from the single member as described above.

The main points of the manufacturing process illustrated in FIGS. 9(a) to 9(c) can be restated in a way as follows. First, a tube with a hollow extending lengthwise is prepared. Then, the tube is shaved to have a curved surface axisymmetric with respect to the axis of the tube, and the tip of the tube is shaved in the circumferential direction of the cylinder. Accordingly, the tube is curved in the circumferential direction and is linearly tilted in the direction of the length. The axisymmetric curved surface constitutes part of the curved surface near the bottom surface of the conical shape and is shaved without bending the hollow. Next, the tip portion of the sampling nozzle is formed by a flat surface passing through a point on the curved surface and a point closer to the root side of the tube (the root side of the CTS nozzle) than the position of the curved surface, that is, a plane linearly machined by a cutting line 903 to surround the hollow and a line of intersection between the flat surface and the curved surface. That is, the tip portion is formed from the portion of the tapered tip of the tube that is obliquely processed to remove one portion.

The process of shaving the curved surface desirably includes a step of forming the tip-side straight portion 502 smaller in outer diameter than the root-side straight portion 501 and forming the root-side tapered portion 503 between the straight portions. The process of shaving the curved surface also includes a step of shaving the tip of the tip-side straight portion 502. In addition, the process of shaving the curved surface desirably includes a step of rounding the acute-angled portion of the tube sandwiched between the plane surrounding the hollow and the hollow because the edge of the cut surface is preferably rounded (by blast polishing or the like, for example) as described above.

Besides the foregoing features, the CTS nozzle of the invention may have other desired shapes. Those skilled in the art can identify the methods of manufacturing the CTS nozzle by adjusting the processing positions and angles of the curved surface and the flat surface of the tip portion. For example, the tip can be positioned closer to the opening than the outside of the range of the thick portion by adjusting the positions on the curved surface included in the processed surface for forming the shaved surface 508. In addition, the angle of the tip portion can be set in a range of 26.0 to 29.5 degrees by adjusting the taper angles of the surfaces.

In the terms of cost reduction, the tip portion is desirably formed from the two curved and flat surfaces, not shaving other surfaces to form a complicated tip shape.

The dimensions of the CTS nozzle 22 described above in relation to the examples are mere exemplification. The length and material of the tapered portion neither have any influence on the effect of reducing the production of rubber chips and suppressing abrasion by the two shaved surfaces of the nozzle tip nor restrict the embodiments of the invention.

REFERENCE SIGNS LIST 10 automatic analyzer
11 reagent container
12 reagent disk
13 reaction disk
14 reagent dispensing mechanism
15 sample dispensing mechanism
21 reagent nozzle
22 CTS nozzle
23 rubber plug
24 sample container
25 sample rack
28 cell
200 general CTS nozzle
201 cut surface
202 opening
203 hollow
204 tip
401 taper
402 cut surface
403 nozzle tip
404 taper end
405 cut end
501 root-side straight portion
502 tip-side straight portion
503 root-side tapered portion
504 tip-side tapered portion 505 hollow
506 nozzle tip (blade
507 nozzle opening
508 cut surface of the nozzle tip
509 edge of the nozzle opening
510 distance from the nozzle's side surface to the blade
511 distance from the end of the nozzle opening to the blade
512 area of the cut surface from the nozzle's centerline to the blade
801 angle A
802 angle B
803 angle C
804 length La
805 length Lb
901 hollow tube
902 machining line of a lathe
903 cutting line

The invention claimed is:

1. A cylindrical sampling nozzle for piercing a sampling container with rubber to aspirate a sample in the container, the nozzle comprising:
   a hollow extending lengthwise of the sampling nozzle, the hollow including an opening for aspirating the sample;
   a first surface disposed at an end of a tube having the hollow, the first surface having a plane surrounding the opening;
   a second surface disposed opposite the first surface; and
   a tip portion of the sampling nozzle formed by an intersection line of the first surface and the second surface, wherein:
   the hollow which is not bent near the tip portion includes the opening;
   the second surface has a curved surface that includes part of a conical shape around a central axis of the cylindrically-shaped sampling nozzle, is curved in a circumferential direction of the cylindrically-shaped sampling nozzle and is tilted linearly with respect to the length of the sampling nozzle; and
   a distance between the tip portion of the sampling nozzle and an end of the second surface on a root side of the sampling nozzle is shorter than a distance between the tip portion of the sampling nozzle and an end of the first surface on a root side of the sampling nozzle.

2. The sampling nozzle according to claim 1, wherein a tilt angle of the first surface is greater than that of the second surface.

3. The sampling nozzle according to claim 1, wherein when seen from the opening side, the tip is positioned within a range of thickness of the sampling nozzle at a position closer to the opening side than to outside the range of thickness.

4. The sampling nozzle according to claim 1, wherein:
the opening of the first surface is elliptically-shaped; and
the plane is shorter at the tip side than at the root side of the sampling nozzle in a major-axis direction of the elliptically-shaped.

5. The sampling nozzle according to claim 4, wherein a difference in area is smaller than or equal to 0.1 mm$^2$ between the second surface and the tip side in the plane divided into the root side and the tip side by a minor axis of the elliptically-shaped.

6. The sampling nozzle according to claim 1, wherein the tip has an angle in a range from 26.0° to 29.5°.

7. The sampling nozzle according to claim 1, further comprising:
   a first straight portion;
   a second straight portion smaller in outside diameter than the first straight portion; and
   a tapered portion disposed between the first straight portion and the second straight portion,
   wherein the tip is disposed at an end of the second straight portion.

8. The sampling nozzle according to claim 7, wherein the first straight portion, the second straight portion, the tapered portion and the tip are made of a same material without being welded to one another.

9. An automatic analyzer having a sample dispensing mechanism provided with the sampling nozzle described in claim 1,
   wherein the sampling dispensing mechanism discharges the sample in a condition that the tip is brought into contact with a bottom of the cell.

* * * * *